United States Patent
Model

(10) Patent No.: US 11,693,074 B2
(45) Date of Patent: Jul. 4, 2023

(54) ELECTRIC CIRCUIT ARRANGEMENT FOR ENERGIZING A MAGNET OF A MAGNETIC RESONANCE IMAGING FACILITY AND MAGNETIC RESONANCE IMAGING FACILITY

(71) Applicant: Siemens Healthcare GmbH, Erlangen (DE)

(72) Inventor: Volker Model, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/527,304

(22) Filed: Nov. 16, 2021

(65) Prior Publication Data
US 2023/0152401 A1  May 18, 2023

(30) Foreign Application Priority Data
Nov. 17, 2020  (DE) ...................... 10 2020 214 442.7

(51) Int. Cl.
| | | |
|---|---|---|
| G01R 33/54 | (2006.01) | |
| H01F 7/06 | (2006.01) | |
| G01R 33/42 | (2006.01) | |
| G01R 33/3815 | (2006.01) | |

(52) U.S. Cl.
CPC ....... *G01R 33/543* (2013.01); *G01R 33/3815* (2013.01); *G01R 33/42* (2013.01); *H01F 7/064* (2013.01)

(58) Field of Classification Search
CPC .. G01R 33/543; G01R 33/3815; G01R 33/42; H01F 7/064
See application file for complete search history.

(56) References Cited

U.S. PATENT DOCUMENTS

| | | | |
|---|---|---|---|
| 2014/0070812 A1* | 3/2014 | Yokoi | G01R 33/48 324/322 |
| 2016/0178717 A1* | 6/2016 | Jiang | G01R 33/3815 324/322 |
| 2017/0261575 A1 | 9/2017 | Model | |

FOREIGN PATENT DOCUMENTS

DE       102016203817 B3       4/2017

\* cited by examiner

*Primary Examiner* — G. M. A Hyder
(74) *Attorney, Agent, or Firm* — Harness, Dickey & Pierce, P.L.C.

(57) ABSTRACT

An electric circuit arrangement for energizing a magnet of a magnetic resonance imaging facility includes a first circuit part, a second circuit part and a control facility. In an embodiment, the first circuit part is designed to generate a direct voltage as an DC link voltage from an alternating voltage and the second circuit part is designed as a current source fed by the DC link voltage. The second circuit part includes a down converter controllable by the control facility, a transformer switchable by the control facility and a rectifier. A primary current is generatable from the DC link voltage via the down converter. The primary current is feedable by a switching facility, switched by the control facility into a primary side of the transformer, and a secondary current for energizing the magnet is generatable via the rectifier connected to a secondary side of the transformer.

19 Claims, 5 Drawing Sheets

ELECTRIC CIRCUIT ARRANGEMENT FOR ENERGIZING A MAGNET OF A MAGNETIC RESONANCE IMAGING FACILITY AND MAGNETIC RESONANCE IMAGING FACILITY

PRIORITY STATEMENT

The present application claims priority under 35 U.S.C. Section 119 to German Patent application 10 2020 214 442.7 filed Nov. 17, 2020, the entire contents of which are hereby incorporated herein by reference.

FIELD

The application generally relates to an electric circuit arrangement for energizing a magnet of a magnetic resonance imaging facility, comprising a first circuit part, a second circuit part and a control facility. In at least one embodiment, the application relates, moreover, to a magnetic resonance imaging facility.

BACKGROUND

As a rule, systems with superconducting magnets are currently used in magnetic resonance tomography. A superconducting magnet can be supplied with the required energy for generating a magnetic field with the desired field strength via a power supply by feeding a current into the magnet. Despite the superconducting design of the magnet it can be necessary to repeat the energization of the magnet after certain periods of time since the field strength generated by the magnet can decrease over time. For example, renewed energizing of the magnet in intervals of approximately one year can be provided.

As a rule, the currents fed into the magnet have a high amperage in the range of several hundred amperes in order to generate sufficiently strong magnetic fields. Furthermore, when energizing the magnet, a high level of accuracy of the adjusted current or a current regulation is required to enable a precise adjustment of a current ramp and/or the desired magnetic field strength. Accordingly, high demands are also placed on the voltage stability of a circuit arrangement used for energizing the magnet since disturbance variables acting on the electric circuit arrangement should have as little effect as possible on the current fed into the magnet.

For energizing a magnet of a magnetic resonance imaging facility it is known to use current supplies with current transformers for measuring the generated current and with resonance transformers, which have large DC reactors on the secondary side for smoothing the generated direct current. The current supplies are sometimes set up at a distance from the magnetic resonance imaging facility and connected by long cables to the magnet since the current transformers and the DC reactors cannot be operated directly next to the magnetic resonance imaging facility owing to the magnetic leakage field.

A power supply can be brought to the magnetic resonance imaging facility during the course of maintenance. This requires a high level of logistical complexity, however, since the power supply has large dimensions and a high weight owing to its capacity and the high current to be generated. The cables used for connecting the power supply to the magnet also contribute to the high level of logistical complexity since, owing to the high amperage, they require large cross-sections and special connecting device (connector) to guarantee contact security for currents in the order of magnitude of several hundred amperes.

A circuit arrangement for the power supply of a magnetic resonance imaging system is known from DE 10 2016 203 817 B3. The system comprises a radio frequency shielding cabinet and at least one basic field magnet, wherein a first circuit facility of the circuit arrangement, which generates a DC link voltage from a grid voltage, is arranged outside of the radio frequency shielding cabinet. A second switching facility of the circuit arrangement is arranged inside the radio frequency shielding cabinet, and this generates a magnetization current for the basic field magnet from the DC link voltage.

SUMMARY

At least one embodiment of the invention is directed to an improved electric circuit arrangement for energizing a magnet of a magnetic resonance imaging facility.

At least one embodiment of the invention is directed to an electric circuit arrangement for energizing a magnet of a magnetic resonance imaging facility, comprising a first circuit part, a second circuit part and a control facility, wherein the second circuit part includes a down converter controlled by the control facility, a transformer switched by the control facility and a rectifier, wherein a primary current can be generated from the DC link voltage via the down converter, and wherein the primary current can be fed by way of a switching facility switched by the control facility into a primary side of the transformer and a secondary current for energizing the magnet can be generated via the rectifier connected to a secondary side of the transformer.

At least one embodiment of the invention is directed to an electric circuit arrangement for energizing a magnet of a magnetic resonance imaging facility, comprising:
 a first circuit part to generate a direct voltage as a DC link voltage from an alternating voltage;
 a second circuit part designed as a current source fed by the DC link voltage; and
 a control facility,
  wherein the second circuit part includes
   a down converter, controllable by the control facility,
   a transformer switchable by the control facility and
   a rectifier,
  wherein a primary current is generatable from the DC link voltage via the down converter,
  wherein the primary current is receivable by a switching facility, switched by the control facility into a primary side of the transformer, and
  wherein a secondary current for energizing the magnet is generatable via the rectifier connected to a secondary side of the transformer.

For an inventive magnetic resonance imaging facility, in at least one embodiment, it is provided that it comprises an inventive electric circuit arrangement of at least one embodiment.

Inventively, in at least one embodiment, it can be provided that the magnetic resonance imaging facility comprises at least one magnet, wherein the second circuit part of the electric circuit arrangement of at least one embodiment is connected to the magnet and is designed for energizing the magnet.

For an inventive magnetic resonance imaging facility, in at least one embodiment, it is provided that it comprises:
 an electric circuit arrangement for energizing a magnet of the magnetic resonance imaging facility, the electric circuit arrangement including a first circuit part to generate a direct voltage as a DC link voltage from an alternating voltage;

a second circuit part designed as a current source fed by the DC link voltage; and a control facility, wherein the second circuit part includes a down converter, controllable by the control facility, a transformer switchable by the control facility and a rectifier, wherein a primary current is generatable from the DC link voltage via the down converter, wherein the primary current is receivable by a switching facility, switched by the control facility into a primary side of the transformer, and wherein a secondary current for energizing the magnet is generatable via the rectifier connected to a secondary side of the transformer.

BRIEF DESCRIPTION OF THE DRAWINGS

Further advantages and details of the present invention can be found in the example embodiments described below and with reference to the drawings, in which.

DETAILED DESCRIPTION OF THE EXAMPLE EMBODIMENTS

Figure 1:
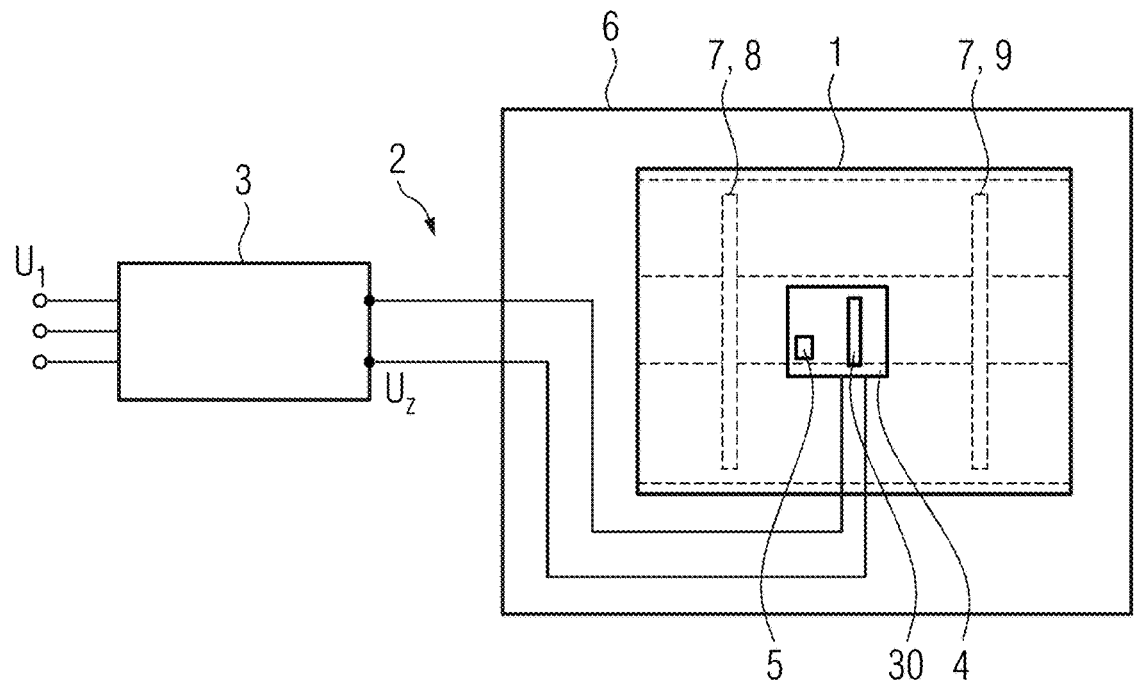
FIG. 1 shows an example embodiment of an inventive magnetic resonance imaging facility.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to an electric circuit arrangement for energizing a magnet of a magnetic resonance imaging facility, comprising a first circuit part, a second circuit part and a control facility, wherein the second circuit part includes a down converter controlled by the control facility, a transformer switched by the control facility and a rectifier, wherein a primary current can be generated from the DC link voltage via the down converter, and wherein the primary current can be fed by way of a switching facility switched by the control facility into a primary side of the transformer and a secondary current for energizing the magnet can be generated via the rectifier connected to a secondary side of the transformer.

In at least one embodiment, the first circuit part of the electric circuit arrangement serves to generate a direct voltage as the DC link voltage from an alternating voltage, in particular a grid voltage. The rectifier of the first circuit part can transform in particular a one-phase, two-phase or three-phase alternating current in order to generate the DC link voltage. The DC link voltage is preferably chosen such that an optimally low intermediate circuit current flows between the first circuit part and the second circuit part.

In at least one embodiment, the second circuit part of the electric circuit arrangement constitutes a current source fed by the DC link voltage, wherein the secondary current generated by the second circuit part can be used as the output current of the electric circuit arrangement for energizing the magnet. Overall, the electric circuit arrangement thus forms one embodiment of a switched-mode power supply.

In at least one embodiment, the second circuit part includes the down converter with which the primary current can be generated from the DC link voltage. The primary current is fed by the switching facility switched by the control facility into the primary side of the transformer, wherein the transformer and the rectifier connected to the secondary side of the transformer transform this primary current into a secondary current with which the magnet of the magnetic resonance imaging facility can be energized.

For this, in at least one embodiment, the control facility switches the switching facility in particular in such a way that the primary current is fed alternately in a different flow direction into the primary side of the transformer. The current generated thereby in each case at the secondary side of the transformer can then be rectified by the rectifier and fed as a secondary current into the magnet. The transformer serves here to transform impedance, so a secondary current with a high amperage can be advantageously generated. Furthermore, a galvanic isolation between the primary side and the secondary side can be advantageously achieved through the use of the transformer.

Energizing the magnet of the magnetic resonance imaging facility with the secondary current serves, in at least one embodiment, to generate a magnetic field of the magnet, in particular a superconducting magnet. For this, the secondary current can have an amperage in the region of several hundred amperes. In at least one embodiment, the inventive design of the second part of the electric circuit arrangement allows a power supply for energizing a magnet of a magnetic resonance imaging facility to form, which allows a precise adjustment of the secondary current for energizing the magnet and thus the magnetic field generated by the magnet. The transformer can already be supplied with a precise primary current through the use of the down converter, facilitating the generation of a secondary current with a high reproducibility. A reproducibility, in order words a deviation between two amperages of the secondary current adjusted at different instants and with the same nominal value, of a few hundred ppm to under one hundred ppm can be achieved in this case. Adjusting a ramp-like current profile of the secondary current is also possible with a high level of accuracy by way of appropriate actuation of the down converter by the control facility.

Furthermore, in at least one embodiment, the second part of the electric circuit arrangement manages with a minimum of magnetizable units, so the arrangement of the second circuit part on or in the magnetic resonance imaging facility, in a region with high magnetic leakage fields therefore, which can lie in the region of several hundred millitesla, is advantageously possible. The second circuit part can be advantageously arranged directly on the magnetic resonance imaging facility. In particular, the second part can be installed in the magnetic resonance imaging facility and thus constitute a permanent component of the magnetic resonance imaging facility. This allows, in particular, assembly of the second circuit part directly on or in the immediate vicinity of the magnet, so connecting device (connector) such as cables or busbars required for connecting the magnet to the electric circuit arrangement can be short.

The first circuit part, in at least one embodiment, can be arranged at a distance from the magnetic resonance imaging facility, in particular outside of/volume surrounding the magnetic resonance imaging facility, and be connected to a second circuit part arranged in or on the magnetic resonance imaging facility by connecting device (connector) for conductance of the intermediate circuit current. The connecting device (connector) can be guided, for example by a feedthrough in a magnetic shield with a feedthrough filter into a shielded space in which the magnetic resonance imaging facility is situated.

As an alternative, in at least one embodiment, it is also possible that both the first circuit part and the second circuit part are arranged outside of this shield, with it being possible for the second circuit part to then be connected to the magnet of the magnetic resonance imaging facility by connecting device (connector) for conducting the secondary current. The connecting device (connector) can also be guided for example by a feedthrough filter in a magnetic shielding into a shielded space in which the magnetic resonance imaging facility is situated.

The control facility, in at least one embodiment, can comprise one or more control devices. The control facility or the control devices can be arranged separately and be connected to the first circuit part and/or the second circuit part. It is also possible that the control facility is integrated wholly or partially in one of the circuit parts, in particular in the second circuit part, with a power supply of the control facility preferably being enabled through a DC-DC converter of the second circuit part converting the DC link voltage.

The circuit topology of the second circuit part, in at least one embodiment, makes it possible for as few as possible electronic units with magnetizable elements to be used, and this advantageously simplifies the possibility for arranging the second circuit part on or in the magnetic resonance imaging facility. Furthermore, electronic components can be used whose magnetizable elements can be as small as possible. This simplifies a magnetic shield of the second circuit part since only individual constituent parts of the second circuit part, for example the transformer and/or a coil of the down converter, have to be magnetically shielded. The fewer magnetic or magnetizable units that have to be shielded, the smaller a magnetic shield can be. A disruptive effect of the magnetizable electric units or the shield thereof on the magnetic fields resulting in the magnetic resonance imaging facility is thus also induced for an arrangement of the second circuit part in the magnetic resonance imaging facility, and thus close to the magnet.

Inventively, in at least one embodiment, it can be provided that an inductor of the down converter is bigger than an inductor of the primary coil of the transformer. The current flow of the primary current is crucially determined thereby due to the inductor of the down converter, so the amperage of the secondary current can advantageously also be adjusted by an actuation of the down converter. The accuracy with which the amperage of the secondary current can be generated can be improved thereby. A profile of the secondary current, for example a ramp-like current profile, can also be adjusted by the actuation of the down converter.

In a preferred embodiment of the invention it can be provided that the switching facility is a full bridge, wherein the primary side of the transformer is switched into the bridge section of a full bridge and the full bridge is connected to the down converter. The current can be fed in different flow directions into the primary side of the transformer, which comprises, for example, a primary coil by the full bridge, which is also referred to as a bridge circuit or H-bridge. For this, the switching elements of the full bridge can be actuated or switched by the control facility.

Inventively, in at least one embodiment, it can be provided that the control facility is designed to feed the primary current by way of the switching facility alternately in a different flow direction into the primary side of the transformer. In particular, the transformer can be operated in an operating cycle in which the primary side of the transformer is energized, without dead time, in each case alternately with the primary current in the different flow directions (also referred to as a 50% duty cycle). In this way, a rectangular current is generated at the primary side of the transformer from the primary current, with the respective amperage of the rectangle corresponding to the positive or negative amperage of the primary current. Operating the transformer in an operating cycle of this kind minimizes the energy stored in the transformer owing to leakage inductances, so the transformer can be advantageously used only for impedance transformation.

The control facility, in at least one embodiment, can switch one or more switching elements of the switching facility with a frequency in the range between 1 kHz and 100 kHz, in particular between 10 kHz and 100 kHz. The flow direction of the primary current at the primary side can be adjusted by the respectively open and closed switching elements, so a rectangular current can be generated. This operating cycle can preferably be permanently adjusted since adjusting the secondary current is advantageously possible by the down converter generating the primary current, so the operating cycle of the transformer advantageously does not have to change in order to adjust an amperage of the secondary current.

In a preferred embodiment of the invention it can be provided that a secondary current with a higher amperage than the primary current can be generated by way of the transformer and/or that the transformer has two secondary coils, which are connected to the rectifier.

The transformer, in at least one embodiment, can have a high transfer factor from a primary coil to at least one secondary coil for the generation of a secondary current with a higher amperage than the primary current, so the amperage of the secondary current can be increased compared with the primary current. It can be provided in particular that the secondary coil or the secondary coils each have a single winding or each have a plurality of single windings connected in parallel, so a high transfer factor, a high ratio between the number of windings of the primary coil to the number of windings of a secondary coil therefore, is possible therefore owing to the secondary-side number of windings of one. The transfer factor of the transformer can be for example between 50:1 and 150:1.

The use of two secondary coils, in at least one embodiment, has the advantage that the rectifier can have a simpler design since in each case a half-wave of the primary current transformed at the secondary side can be tapped by way of the two secondary coils. This reduces the number of switching elements or diodes required to form the rectifier.

The rectifier connected to the secondary side of the transformer for generation of the secondary current, in at least one embodiment, can be configured as an active rectifier or a passive rectifier. An active rectifier can comprise one or more switching elements and be actuated in particular by the control facility. A passive rectifier can be formed from one or more diodes, so the secondary current for energizing the magnet can be generated from the current at the secondary side of the transformer.

For smoothing the secondary current it is possible, in at least one embodiment, that one or more capacitors are arranged at the output side of the rectifier. This capacitor or these capacitors can also be a constituent part of the down converter, with it being advantageously possible to achieve smoothing of the secondary current by way of the arrangement of the capacitors at the output side of the rectifier. Furthermore, the circuit design of the second circuit part can be simplified by the arrangement of at least one capacitor of the down converter at the output side of the rectifier.

In a preferred embodiment of the invention it can be provided that the electric circuit arrangement comprises a first current measuring device or circuit for measuring the primary current and a second current measuring device or circuit for measuring the secondary current, wherein the control facility is configured to actuate the down converter as a function of at least one first measured value of the first current measuring device or circuit describing the primary current and at least one second measured value of the second current measuring device or circuit describing the secondary current. The circuit topology of the second circuit part advantageously makes it possible for the primary current and/or the secondary current to be measured without the use of expensive current transformers, which cannot be operated in a high magnetic leakage field.

The control facility, in at least one embodiment, can actuate the down converter both as a function of the first measured value of the first current measuring device or circuit describing the primary current and of the measured value of the second current measuring device or circuit describing the secondary current. In this way, different effects, which affect the secondary current, can be compensated or eliminated in different ways by actuation of the down converter. This advantageously makes it possible that the secondary current can be regulated with a high level of accuracy or reproducibility in the region of less than one hundred ppm. Energizing the magnet of the magnetic resonance imaging facility can be precisely undertaken thereby. Apart from generating a precise maximum value of the amperage, precise adjustment of a ramp-like current profile of the secondary current is also possible by way of the actuation of the down converter by the control facility.

For this, it can inventively be provided, in at least one embodiment, that the control facility is designed for regulation of the primary current as a function of the first measured value and for adaptive tracking of the primary current as a function of the second measured value. A two-stage current regulation can be advantageously achieved by the use of the first current measuring device or circuit and the second current measuring device or circuit. A current sensor with a higher bandwidth, accordingly with a lower integration time therefore, than the second current measuring device or circuit can be used in particular as the first current measuring device or circuit. Accordingly, the second current measuring device or circuit has a lower bandwidth and thus a higher integration time than the first current measuring device or circuit.

The primary current, in at least one embodiment, can be regulated as a function of the first measured value, so disturbance variables acting on the primary current can already be compensated more quickly. Such a disturbance variable can be, for example, a fluctuation in the DC link voltage, which is generated by the first circuit part. A fluctuation in the DC link voltage can result, for example, owing to grid fluctuations if the first circuit part rectifies a grid alternating voltage. This regulation of the primary current also contributes to the fact that the secondary current can be generated significantly more precisely than the output current.

The secondary current, in at least one embodiment, can be measured in particular in the framework of a very precise absolute value measurement with the second current measuring device or circuit. The direct measurement of the secondary current makes it possible, for example, to compensate comparatively slow fluctuations when generating the secondary current in the transformer and/or the rectifier by adaptive tracking of the primary current. With adaptive tracking, for example the desired value of the primary current necessary for generating a predefined amperage of the secondary current can be adjusted to correct the deviation in the amperage of the secondary current established by way of the second measuring device or circuit. In this way, fluctuations in the transformation ratio between the primary current and the secondary current can be compensated in particular.

For example, a sigma-delta modulator or a sigma-delta converter, in at least one embodiment, can be used as the first current measuring device or circuit and/or as the second current measuring device or circuit. The use of other types of current measuring devices or circuits as the first current measuring device or circuit and/or as the second current measuring device or circuit is also possible, wherein current measuring device or circuit without magnetizable elements can preferably be used.

For an inventive magnetic resonance imaging facility, in at least one embodiment, it is provided that it comprises an inventive electric circuit arrangement of an embodiment.

Inventively, in at least one embodiment, it can be provided that the magnetic resonance imaging facility comprises at least one magnet, wherein the second circuit part of the electric circuit arrangement of an embodiment is connected to the magnet and is designed for energizing the magnet.

The second circuit part, in at least one embodiment, can be inventively arranged in and/or on a housing of the magnetic resonance imaging facility. The second circuit part forms a constituent part of the magnetic resonance imaging facility and is integrated in it or arranged inside the magnetic resonance imaging facility. The first circuit part is arranged, in particular, at a distance from the magnetic resonance imaging facility, in particular outside of a shield surrounding the entire magnetic resonance imaging facility.

It is possible, in at least one embodiment, that the second circuit part has at least one DC-DC converter, which from the DC link voltage fed into the second circuit part comprises at least one supply voltage for the operation of further components of the magnetic resonance imaging facility and/or the control facility of the circuit arrangement. In this way, a power supply of further constituents parts of the magnetic resonance imaging facility and/or the electric circuit arrangement can also be achieved by the electric circuit arrangement.

Inventively, in at least one embodiment, it can be provided that the magnetic resonance imaging facility has a patient receptacle extending in a longitudinal direction, a magnetic shielding element and a coil arrangement comprising at least two coil rings, wherein the two coil rings are arranged offset along the longitudinal direction and the coil arrangement is designed to form a magnetic field in an internal volume at least partially comprising the patient receptacle and partially surrounded by the coil rings, wherein the shielding element and at least one electric component of the second circuit part of the electric circuit arrangement are arranged outside of the internal volume, centrally between the coil rings in the longitudinal direction, wherein the shielding element shields the electric component.

The coil arrangement or the coil rings of the coil arrangement constitute, in at least one embodiment, a part of the magnet of the magnetic resonance imaging facility. The coil rings can be connected to the second circuit part in such a way that the secondary current can be used for energizing the coil rings and thus for generation of the magnetic field of the coil arrangement. The coil arrangement comprising the at least two coil rings serves to generate a magnetic field, which is homogeneous preferably at least in certain sections in an image acquisition region of the patient receptacle, also referred to as the "field of view", to enable magnetic resonance imaging there.

In at least one embodiment, the coil rings arranged offset along the longitudinal direction correspond in terms of their active principle at least substantially to a Helmholtz coil, by way of which, sectionally, a homogeneous magnetic field can be generated in the region of the internal volume at least partially enclosed by the coil rings. This occurs in that the magnetic fields generated by the two coil rings structurally overlap in the region of a center line of the internal volume enclosed by the coil rings. For this, a current can flow through the coil rings in the same direction in each case.

In a region outside of the internal volume and centrally between the coil rings, in at least one embodiment, the magnetic fields of the two coil rings destructively overlap, however, so overall a lower magnetic field strength forms there. An improved shielding effect due to the shielding element, and thus better protection of the electric component shielded by the shielding element, is brought about by the inventive arrangement of the shielding element and the electric component for shielding in this region.

In at least one embodiment, the positioning of the shielding element also relates to the arrangement of the coil rings of the coil arrangement used for generation of the magnetic field and can also be applied in the case of more than two coil rings if they are arranged for example symmetrically around a center point or center line or a center plane. The coil rings can be arranged, for example, in each case around a support ring, also referred to as a buttress ring, with the coil rings each being formed for example by an electric conductor, in particular a superconductor, wound around the support ring. It is possible that the coil arrangement or the magnet of the magnetic resonance imaging facility comprises further coils, which serve for example to improve the homogeneity of the magnetic field generated by the coil arrangement in the region of the patient receptacle and which are energized, in particular, also by the secondary current generated by the electric circuit arrangement. The longitudinal direction, along which the coil rings are arranged offset, corresponds to the longitudinal direction of the patient receptacle and is also referred to as the z-direction.

Advantageously, in at least one embodiment a local shield, which shields only the at least one electric component for shielding, can be generated by the shielding element. The shielding element can be configured thereby in the order of magnitude of the electric component for shielding. The shielding element extends in particular in the longitudinal direction only over a short part of the section between the coil rings. The shielding element can be short in design in the radial direction as well. This makes it possible to achieve that the shielding element is exposed to only a low gradient of the leakage field, of the magnetic field of the coil arrangement outside of the internal volume therefore.

In at least one embodiment, in the circumferential direction of the coil rings the extension of the shielding element is basically not limited since the region with the low field strength extends annularly between the coil rings for reasons of symmetry. The shielding element preferably also extends in the circumferential direction only over part of the circumference, however, to enable a compact design of the shielding element. An extension of the shielding element tangentially to the circumferential direction of the coil rings is also conceivable. The use of the shielding element makes it advantageously possible to dispense with the use of large shields.

Inventively, in at least one embodiment, it can be provided that the electric component is the transformer, a coil of the down converter and/or a DC-DC converter of the second circuit part. The coil of the down converter can have, in particular, a magnetizable core, for example a ferrite core, so it has to be shielded from the magnetic field generated by the coil arrangement of the magnetic resonance imaging facility. Accordingly, the transformer can also have a magnetizable core, which couples the primary coil to the secondary coil, so the transformer also has to be shielded from the magnetic field of the magnetic resonance imaging facility. A DC-DC converter of the second circuit part, which serves, for example, to operate further components of the second circuit part and/or the magnetic resonance imaging facility, can also be shielded by the shielding element, in particular if it comprises a magnetizable component. The further constituent parts of the second circuit part can be arranged outside of the shielding element since they can be configured in such a way that they can also be operated in a magnetic leakage field of the coil arrangement or of the magnet of the magnetic resonance imaging facility.

The shielding element, in at least one embodiment, advantageously makes it possible that in particular the transformer can be arranged close to the magnet of the magnetic resonance imaging facility without undesirable effects occurring during operation of the electric component, for example a complete magnetization of a core of the transformer, due to the magnetic leakage field of the coil rings. Correspondingly, this also apples to a coil comprising a magnetizable core and/or a DC-DC converter comprising a magnetizable element. Forces, which are generated by the magnetic field of the magnetic resonance imaging facility, acting on these electric components can also advantageously be minimized. Furthermore, the effect, which the shielding element has on the field generation in the magnetic resonance imaging facility and thus also on imaging, can also advantageously be reduced.

Inventively, in at least one embodiment, it can be provided that the shielding element at least partially surrounds a shielding volume, which is shielded by the shielding element, wherein the electric component is arranged in the shielding volume. This makes it possible for the electric component, which is for example a constituent part of an electric circuit arrangement comprising a plurality of components, to be magnetically shielded in the shielding volume. The shielding element is formed in such a way that in the shielding volume it brings about a magnetic shielding of the electric component from the leakage field of the coil arrangement, the magnetic field generated by the coil arrangement outside of the internal volume, therefore.

Inventively, in at least one embodiment, it can be provided that the shielding element has a U-shaped cross-section, with the shielding element surrounding the shielding volume on at least three sides. The arrangement of the shielding element in relation to the coil rings of the coil arrangement advantageously makes it possible for complete encasing of the shielding volume by the shielding element to be omitted. This reduces the quantity of material required to form the shielding element, and this has an advantageous effect in particular on the homogeneity of the magnetic field generated by the coil arrangement. Advantageously, shielding of the shielding volume with an optimally low quantity of material or an optimally low mass of the shielding element can thus be achieved.

The shielding volume, in at least one embodiment, is surrounded on at least three sides by the U-shape of the cross-section of the shielding element, namely by the closed side of the U-shaped cross-section opposing the open side and by the two legs of the U-shaped cross-section. The shielding element can be arranged in particular in such a way that the legs of the U-shaped cross-section are at a distance from each other along the longitudinal direction and extend in the radial direction of the coil rings.

Inventively, in at least one embodiment, it can be provided that, as an alternative, the shielding element is also cup-shaped, box-shaped or trough-shaped, with the shielding element completely surrounding the shielding volume with the exception of the open side of the shielding element. A cup-shaped, box-shaped or trough-shaped shielding element can have a base section from which, depending on cross-section geometry, one or more wall sections extend, with the shielding volume being encompassed or delimited by the base section and the wall sections. Apart from a rectangular cross-sectional shape with four wall sections, oval or round shapes with just one wall section are also conceivable. Opposite the base section the shielding element has an open side. This open side make it possible, for example, that an electric component secured to a flat carrier element can be arranged in the shielding volume of the shielding element pushed over it, so, with the exception of the open side, the electric component is completely surrounded by the shielding element. The base section can be straight or arcuate, wherein with an arcuate section the wall sections extend from the concave side of the base section or the internal volume enclosed by the shielding element adjoins the concave side of the base section.

Compared with a shielding element with a U-shaped cross-section, in at least one embodiment a cup-shaped, box-shaped or trough-shaped shielding element surrounds the internal volume further, so, depending on the field profile of the leakage field for shielding, an even better shielding can be achieved.

In at least one embodiment, the open side of the U-shaped cross-section or the open side of the shielding element can inventively point toward the internal volume. The closed side of the U-shaped cross-section or a base section of the U-shaped shielding element, which opposes the open side, or a base section of a cup-shaped, box-shaped or trough-shaped shielding element, which opposes the open side, accordingly points away from the internal volume and is thus at a greater distance from the patient receptacle or the field of view in the patient receptacle. This further reduces the effect which the shielding element has on the magnetic field generation by way of the coil arrangement.

In a preferred embodiment of the invention it can be provided that an air gap is formed and/or an a magnetic distance element is arranged between the electric component and the shielding element. The air gap and/or the a magnetic distance element prevent a magnetic flux guided by the shielding element from entering the electric component. A magnetic transfer resistance between the shield and the electric component is increased by the formation of the air gap or the arrangement of the a magnetic distance element between the shielding element and the electric component therefore, in order to improve the shielding effect of the shielding element.

Inventively, in at least one embodiment, it can be provided that the shielding element is longer in the circumferential direction or tangentially to the circumferential direction of the coil rings than in the longitudinal direction and/or in the radial direction of the coil rings. Preferably, the shielding element extends with its longest extension in the direction of the circumference of the coil rings or tangentially to the direction of the circumference of the coil rings, therefore. In particular, the narrow design of the shielding element relative to the longitudinal direction means that the shielding element can extend only in a region with a low gradient of the leakage field. It is possible that the shielding element extends around the entire circumference of the internal volume, so the shielding element has an annular shape. It is also possible, however, that the shielding element extends over only a section of this circumference, with the shielding element being straight in this circumferential direction or being bent, in particular in accordance with the radius of this circumference.

In at least one embodiment, a shielding element with U-shaped cross-section is preferably arranged in such a way that the legs of the U-shaped section are spaced apart in the longitudinal direction and extend in the radial direction of the coil rings. The open side of the U-shaped cross-section extends in the longitudinal direction and in the circumferential direction and preferably points toward the internal volume. A cup-shaped, box-shaped or trough-shaped shielding element is preferably likewise arranged in such a way that the open side of the shielding element points toward the internal volume.

In at least one embodiment, the shielding element can have, for example, a length between 5 cm and 25 cm, in particular of 10 cm, in the radial direction. The shielding element can have a length between 5 cm and 25 cm, in particular of 10 cm, in the longitudinal direction too. The shielding element can have a length between 15 cm and 50 cm, in particular of 25 cm, in the circumferential direction of the coil rings or tangentially to the circumferential direction of the coil rings.

In at least one embodiment, inventively it can be provided that the shielding element is made at least partially from iron. For example, the shielding element can be made from constructional steel and have a material thickness or a wall thickness between 5 mm and 15 mm, in particular of 10 mm. The use of a shielding element made at least partially from iron has the advantage that iron has a higher saturation magnetization compared to other materials for the magnetic shield. This prevents a saturation of the magnetization of the shielding element with the arrangement of the shielding element between the coil rings. In particular, since magnetic flux densities in the range between 50 mT and 500 mT can exist in these regions even in air, a high saturation magnetization of the shielding element is desirable.

In a preferred embodiment of the invention it can be provided that the magnetic resonance imaging facility has an inner cover, which surrounds the coil arrangement, with the shielding element being arranged on the inner cover. The inner cover can have, for example, at least substantially the form of a cylinder jacket. The inner cover can surround, for example, a coolant required for generation of a superconductivity in the coil arrangement. The cover of the shielding element can be arranged on or secured to an outer side, in other words a side of the inner cover located opposite the internal volume. The fastening can be direct or indirect by way of at least one carrier element.

In this way, in at least one embodiment, the shielding element and the at least one electric component shielded by the shielding element can be arranged in an interior of the magnetic resonance imaging facility. The inner cover, which surrounds the coil arrangement, can for its part be covered by an external device cover of the magnetic resonance imaging facility, which with arrangement of the shielding element on the inner cover, also encases the shielding element and the electric component arranged therein and/or an electric circuit arrangement comprising the electric component. With an at least substantially cylinder jacket-like design of the inner cover, the longest extension of the shielding element can extend in particular in the circumferential direction or tangentially to the circumferential direction of the inner cover, with it being possible for the shielding element to be arranged in particular at any position of the inner cover or at any position around the inner cover.

FIG. 1 illustrates an inventive magnetic resonance imaging facility 1. The magnetic resonance imaging facility 1 comprises an electric circuit arrangement 2, which is composed of a first circuit part 3 and a second circuit part 4 and a control facility 5. The magnetic resonance imaging facility 1 is surrounded by a shield 6, which shields the magnetic fields generated by the magnetic resonance imaging facility 1. The first circuit part 3 of the electric circuit arrangement 2 is arranged outside of this shield 6 and can be situated, for example, in a plant room adjoining the shield 6. The second circuit part 4 and the control facility 5 are situated inside the shield 6 and are configured directly as a part of the magnetic resonance imaging facility 1. The second circuit part 4 and the control facility 5 can be arranged, for example, in an interior of a housing encasing the magnetic resonance imaging facility 1, as will be described in more detail below.

The first circuit part 3 serves to generate a direct voltage as the DC link voltage UZ from an alternating voltage U1. The second circuit part 4 is designed as a current source fed by the DC link voltage UZ, with an output current of the second circuit part 4 serving to energize a magnet of the magnetic resonance imaging facility 1. This magnet can be formed from a coil arrangement 7, which comprises two coil rings 8, 9, or can comprise the coil arrangement 7 with the coil rings 8, 9. The magnet of the magnetic resonance imaging facility 1 is in particular superconducting, with it being possible for the magnet to be energized by the electric circuit arrangement 2 in order to generate a magnetic field by way of currents flowing through the superconductor. The magnet can be energized again, for example by the application of a ramp-like current profile, by way of the electric circuit arrangement, for example when the magnetic field strength, which is generated by the magnet or the coil rings 8, 9, declines.

Figure 2:
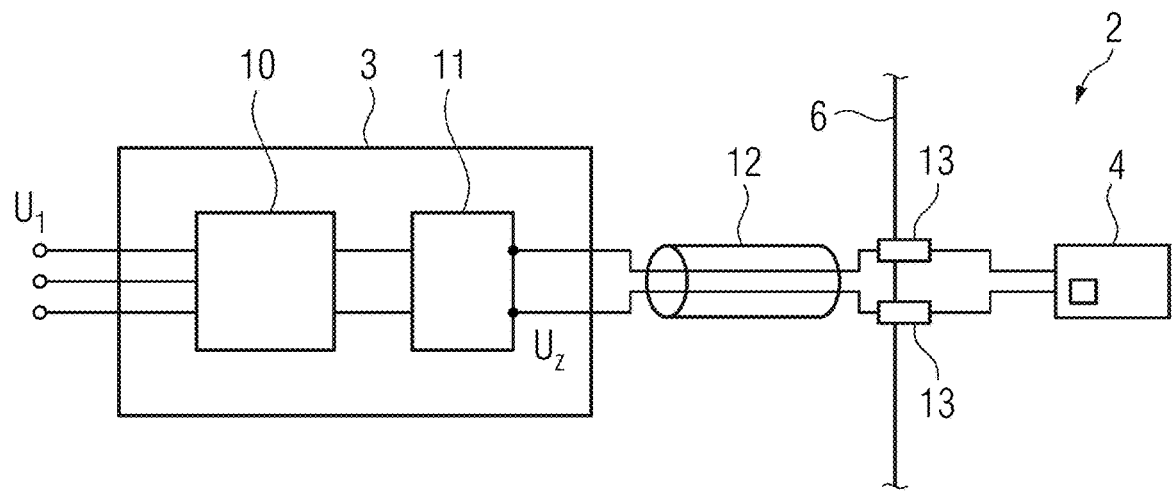
FIG. 2 shows a first example embodiment of an inventive electric circuit arrangement.

FIG. 2 illustrates an example embodiment of the electric circuit arrangement 2 of the magnetic resonance imaging facility 1. The first circuit part 3 comprises a transformer 10, which transforms the input-side alternating voltage U1 and feeds it into a rectifier 11. One or more phases of the alternating voltage U1, which is, for example, a three-phase grid voltage, can be rectified by the rectifier 11. The rectifier 11 can comprise, in particular, an active or a passive power factor correction filter (also referred to as a "power factor correction" or PFC). The DC-DC converter 11 generates the DC link voltage UZ, via which the second circuit part 4 is fed. The DC-DC converter 11 can be configured as a step-up converter or as a boost converter, which increases the DC link voltage UZ, so only a comparatively low intermediate circuit current flows between the first circuit part 3 and the second circuit part 4.

The first circuit part 3 is connected to the second circuit part 4 by a connecting device (connector) 12 designed, for example, as a two-core cable. The DC link voltage UZ is applied to the connecting device (connector) 12, so the second circuit part 4 can be fed by way of the intermediate circuit current. The second circuit part 4 is connected to the first circuit part 3 by the connecting device (connector) 12 and a filter mechanism 13 arranged in the shield 6 for filtering electromagnetic interference (EMI filter).

Figure 3:
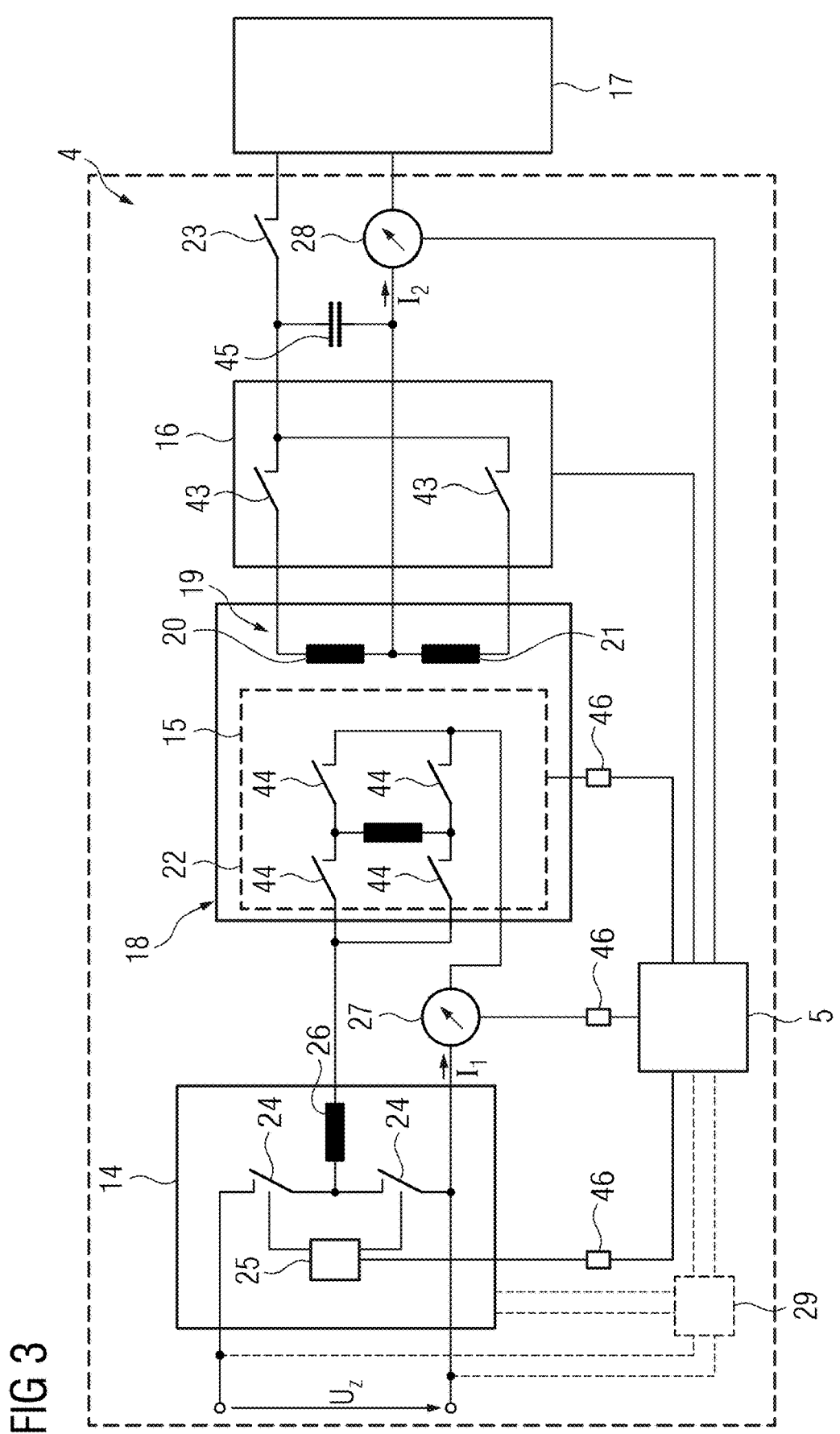
FIG. 3 shows a detailed view of the second circuit part of the electric circuit arrangement.

FIG. 3 illustrates a detailed view of the second circuit part 4 of the electric circuit arrangement 2. The second circuit part 4 comprises a down converter 14, a transformer 15, a switching facility 22 designed as a full bridge and a rectifier 16. Also illustrated schematically is the magnet 17 of the magnetic resonance imaging facility 1, which can be energized by the second circuit part 4.

A primary current I1 fed into a primary side 18 of the transformer 15 is generated via the down converter 14 from the DC link voltage UZ. The primary current I1 can be fed by way of the switching facility 22, designed as a full bridge, in different flow directions into the primary side 18 of the transformer 15, which is switched into the bridge section of the full bridge. For this, the switching facility 22 can be clocked by the control facility 15. The control facility 5 is designed to feed the primary current I1 by way of the switching facility 22 alternately in a different flow direction into the primary side 18 of the transformer 15.

An operating cycle can be adjusted by the control facility 5 in which the primary current I1 is supplied to the primary side 18 alternately and without dead time in the different flow directions (50% duty cycle). In this way, an almost ideal rectangular current is generated at the primary side 18, so the amount of energy stored in the transformer 15 can be minimized during the current transfer of the primary current I1. The operating cycle can be adjusted independently of an amperage of the secondary current I2 that is to be generated since the amperage of the secondary current I2 can be adjusted by way of the primary current I1 or the down converter 14. For generation of the operating cycle, the switching elements 44 of the full bridge, which are configured for example as transistors, in particular as metal oxide semiconductor field effect transistors (MOSFETs) or bipolar transistors, can be actuated with a frequency between 1 kHz and 100 kHz, in particular between 10 kHz and 100 kHz, with the capacity utilization over time resulting from the ratio of the durations with in each case open and in each case closed switching elements, in other words from the times during which the primary current I1 is fed into the primary side 18 of the transformer 15, and the times during which the primary current I1 is not fed into the primary side 18 of the transformer 15.

The transformer 15 serves to transform impedance and has a high transfer factor or a high transfer ratio, in particular between 50:1 and 150:1, between the primary side 18 and the secondary side 19. The secondary coils 20, 21 can have, in particular, in each case a single winding or in each case a plurality of windings connected in parallel, so there is only one winding on the secondary side. A current can be generated at the secondary side by the high transfer ration, the amperage of which current is much greater than that of the primary current I1 at the primary side 18 of the transformer 15, so a direct current with higher amperage than the secondary current I2 can be generated by the rectifier 16.

The secondary side 19 of the transformer 15 is connected to the rectifier 16 for generation of the secondary current I2, which is fed into the magnet 17. In this example embodiment, the secondary side 19 of the transformer 15 comprises two secondary coils 20, 21, which are designed for tapping in each case a half-wave of the current induced by the primary current I1 at the secondary side 19 of the transformer 15. In this example embodiment, the rectifier 16 is designed as a plurality of switching elements 43 for rectifying the current tapped at the secondary side 19 of the transformer. The switching elements 43 are configured for example as transistors, in particular as metal oxide semiconductor field effect transistors (MOSFETs) or bipolar transistors. Furthermore, the rectifier 16 comprises a switch 23 to switch off the secondary current I2. A capacitor 45, which serves to smooth the secondary current I2, is arranged at the output side of the rectifier 16. The capacitor 45 is a capacitor of the down converter 14, with the arrangement of the capacitor 45 at the output side of the rectifier 16 making a compact circuit design possible.

The down converter 14 can have one or more switching elements 24, which can be switched, for example, by a bootstrap circuit 25 connected to the control facility 5. Furthermore, the down converter 14 comprises an inductor 26, which is bigger than the inductor of the primary coil 18 of the transformer 15. In this way, the primary current I1 fed into the transformer 15 is largely determined by the down converter 14, so the secondary current I2 can also be adjusted by an adjustment of the primary current I1 by way of the control facility 5.

The second circuit part 4 of the electric circuit arrangement 2 also comprises a first current measuring device or circuit 27 by which a first measured value describing the primary current I1 can be detected. Furthermore, the second circuit part 4 comprises a second measuring device or circuit 28 by which a measured value describing the secondary current I2 can be detected. The control facility 5 is designed to actuate the down converter 14 as a function of the measured values of the first current measuring device or circuit 27 and the second current measuring device or circuit 28.

The current measuring device or circuit 27 is designed for a current measurement with a high bandwidth and consequently lower integration time, so disruptions such as grid fluctuations of the alternating voltage U1, which likewise cause fluctuations in the DC link voltage UZ, can be compensated by the measurement of the primary current I1 and a corresponding regulation of the down converter 14. The first current measuring device or circuit 27 can be configured, for example, as a sigma-delta modulator or as a sigma-delta converter. The use of a different type of current sensor to the first current measuring device or circuit 27 is also possible.

The second current measuring device or circuit 28 is designed for a current measurement with a low bandwidth and high integration time to enable a very precise absolute value measurement of the secondary current I2 fed into the magnet 17. The down converter 14 can be adaptively tracked by the control facility 5 to adaptively adjust, for example, fluctuations in the generation of the secondary current I2, which trace back to a fluctuating coupling ratio in the transformer 15 and/or to the rectifier 16. This type of current regulation makes it advantageously possible to dispense with current sensors, which cannot be operated in a magnetic leakage field. Furthermore, a high absolute value accuracy of the secondary current I2, in particular with deviations only in a region of a few hundred ppm of the amperage of the secondary current I2, is thus achieved. A high reproducibility of a current or an amperage can also be achieved, with it being possible for the deviation between the amperages of two secondary currents adjusted to the same nominal value to be, in particular, less than one hundred ppm. The second current measuring device or circuit 28 can also be configured, for example, as a sigma-delta modulator or as a sigma-delta converter. The use of a different type of current sensor as the second current measuring device or circuit 28 is also possible.

The actuation of the down converter 14, the switching facility 22 and the connection to the first current measuring device or circuit 27 to the control facility 5 can take place by way 46 of galvanic isolation, for example by way of optocouplers and/or other galvanically isolating transformers, so the control facility 5 and the section of the second circuit part 4 from the secondary side 19 of the transformer 15 can be completely galvanically isolated from the further components located at the input side, in other words in particular of the primary side 18 of the transformer 15, the down converter 14 and the first circuit part 3.

The second circuit part 4 of the electric circuit arrangement 2 can have one or more DC-DC converters 29, which is used for energizing the switching elements 24 of the down converter 14, the control facility and the current measuring device or circuit 27 and possible further components of the second circuit part 4. In addition it is also possible that the second circuit part 4 has further DC-DC converters (not shown here), which can energize further components of the electric circuit arrangement 2 and/or the magnetic resonance imaging facility 1 from the DC link voltage UZ.

The circuit topology of the second circuit part 4 makes it advantageously possible to use only a minimum of units with magnetizable elements. Magnetizable elements can comprise, in particular, the inductor 26 of the down converter 14, which is designed, for example, as a coil with a magnetizable ferrite core, and/or be the DC-DC converter 29. The transformer 15 can also have a magnetizable core, so shielding of the inductor 26, the transformer 15 and/or a possibly present DC-DC converter 29 can be required with an arrangement of the second circuit part 4 on the magnetic resonance imaging facility 1.

Figure 4:
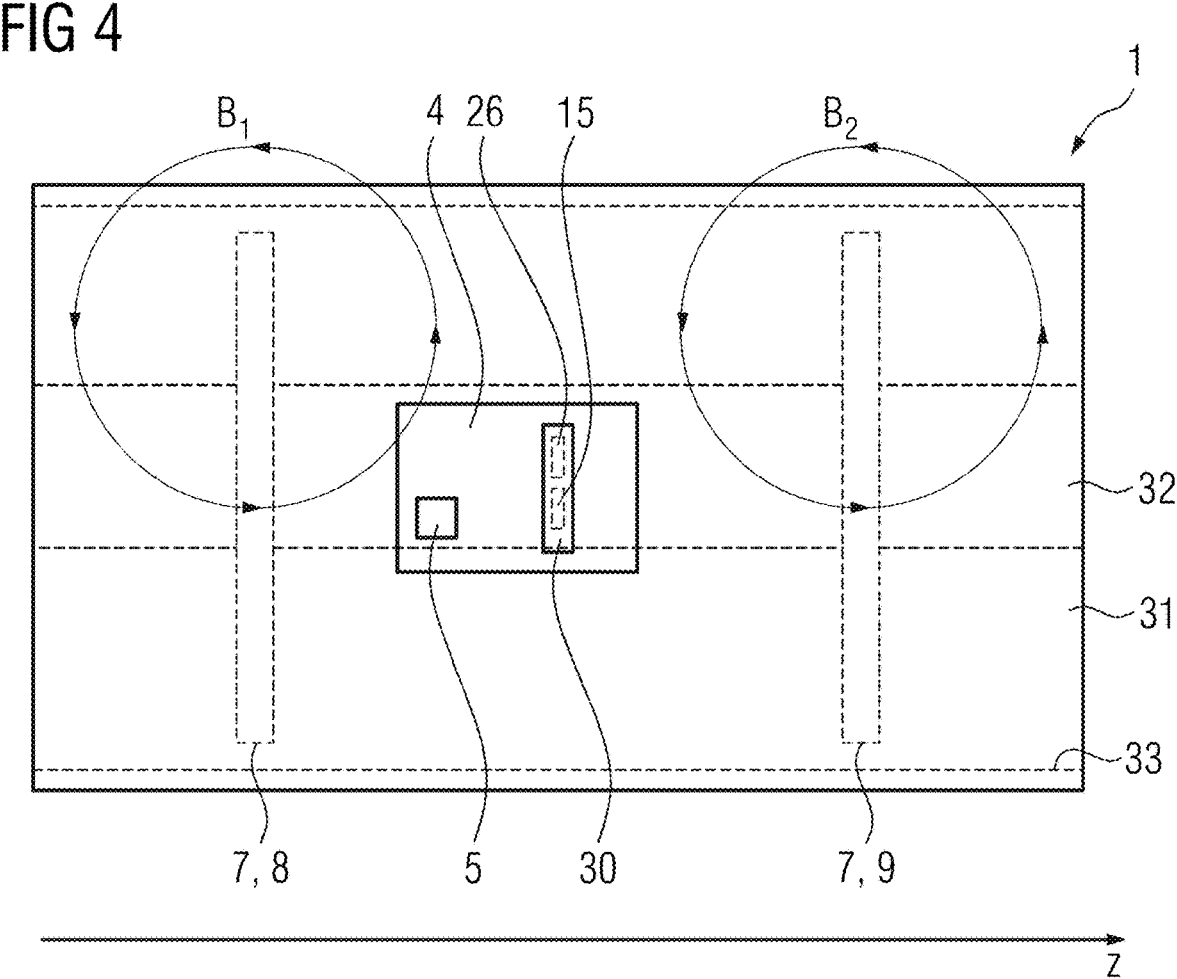
FIG. 4 shows a view of the arrangement of the second circuit part on the magnetic resonance imaging facility.

As is illustrated in FIG. 4, the inductor 26 of the down converter 14 and the transformer 15 are arranged in such a way that they are shielded by a shielding element 30 of the magnetic resonance imaging facility 1. The second circuit part 4 of the electric circuit arrangement 2 is arranged in or on a housing of the magnetic resonance imaging facility 1 and thus in the region of a leakage field of the magnetic resonance imaging facility 1.

The shielding element 30 and the electric components shielded by the shielding element 30, namely the inductor 26 and the transformer 15, are arranged in such a way that the shielding element 30 and the electric components are arranged centrally between the two annular coils 8, 9 of the coil arrangement 7. In this way, the shielding element 30 makes a particularly good shielding possible. Running in the central region between the annular coils 8, 9 are the magnetic fields or the magnetic flux densities B1 and B2, which are generated by the coil rings 8 or 9, as illustrated in different directions, so they are at least partially cancelled out.

Figure 5:
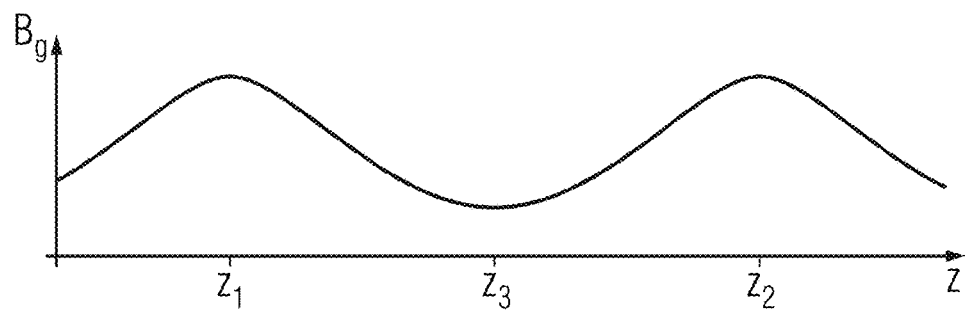
FIG. 5 shows a diagram to illustrate the function of the shielding element of the magnetic resonance imaging facility.

This is schematically illustrated in FIG. 5 by the characteristic of an overall magnetic flux density BG, which is composed of the magnetic flux density B1 of the first coil ring 8 and the magnetic flux density B2 of the second coil ring 9. Between the position z1 of the first coil ring 8 and the position z2 of the second coil ring 9 only a low magnetic flux density BG is attained in the central position z3 between the coil rings 8, 9, in which the shielding element 30 is arranged, with the region with the low flux density being annular for reasons of symmetry and being located centrally between the coil rings 8, 9.

The annular coils 8, 9 of the coil arrangement 7 are designed to form, in an internal volume 31 at least partially enclosed by the coil rings 8, 9, which volume comprises a patient receptacle 32 extending in the longitudinal direction (z-direction), at least in certain sections an, in particular, homogeneous magnetic field. The shielding element 30 is arranged outside of the internal volume, centrally between the coil rings 8, 9, so the total flux density BG acting on the shielding element is as low as possible. The transformer 15 and the inductor 26 as shielded electric components are also arranged centrally between the coil rings 8, 9, so they are shielded by the shielding element.

The shielding element 30 and/or the second circuit part 4 can be arranged in particular on an internal cover element 33 of the magnetic resonance imaging facility 1 surrounding the coil arrangement 7. The internal cover element 33 can have, for example, at least substantially the form of a cylinder jacket, with the shielding element 30 and the second circuit part 4 being arranged and/or secured to the outside of the internal cover element 33. The internal cover element 33 and the second circuit part 4 as well as the shielding element 30 can be encased by an external housing of the magnetic resonance imaging facility 1, so the second circuit part 4 and the shielding element 30 are integrated in the magnetic resonance imaging facility 1.

Figure 6:
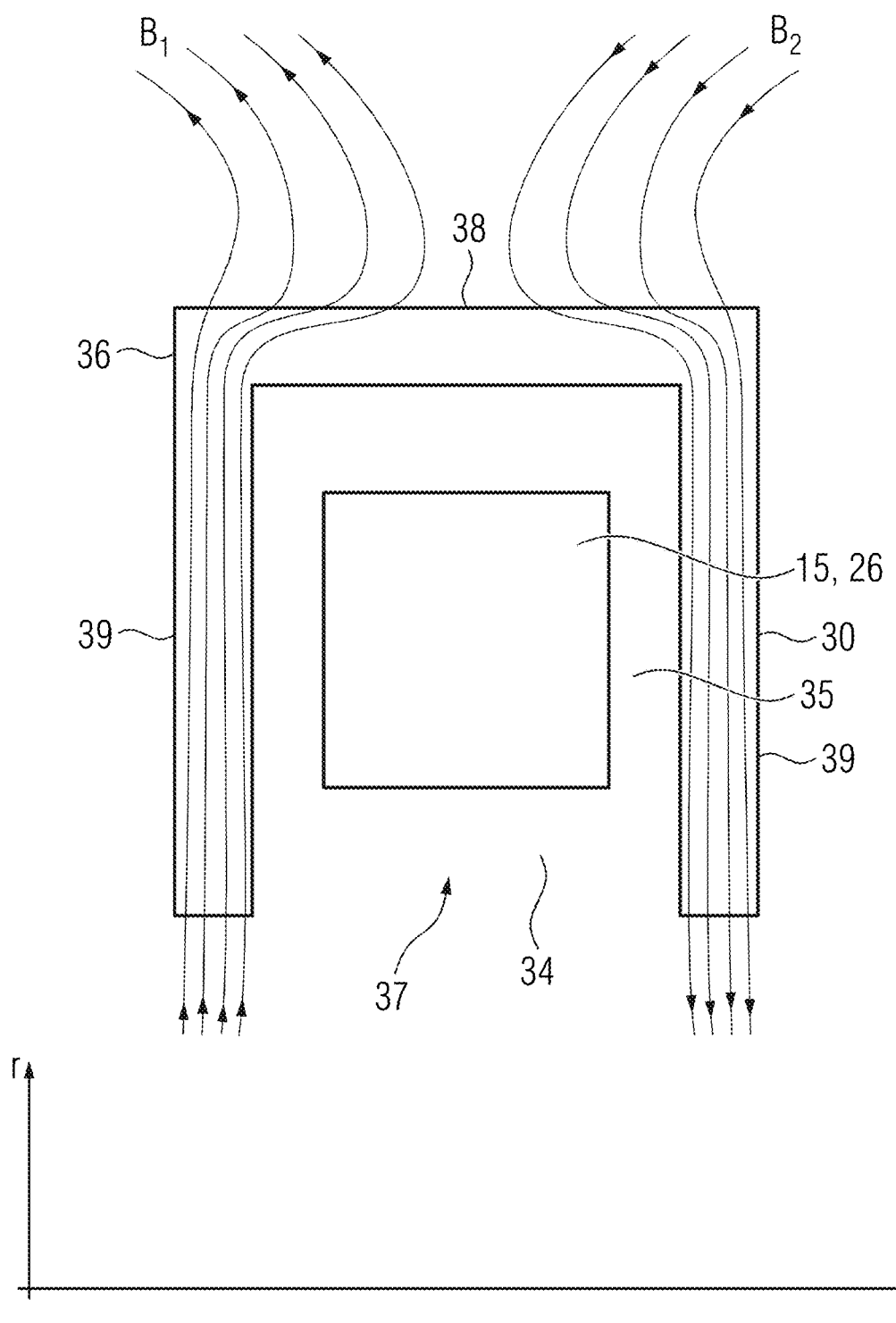
FIG. 6 shows a cross-section of an example embodiment of a shielding element of the magnetic resonance imaging facility.

FIG. 6 illustrates a cross-section of an example embodiment of the shielding element 30. The shielding element 30 at least partially surrounds a shielding volume 34 in which the electric components 15, 26 is arranged. An air gap 35 is formed between the electric components 15, 26 and interior of the shielding element 30. The air gap 35 prevents the magnetic flux conducted by the shielding element, which flux is schematically illustrated by the field line sections of the magnetic fluxes B1 and B2, from passing into the electric components 8. In addition or as an alternative to the air gap 35, an magnetic distance element can also be arranged between the shielding element 30 and the electric components 15, 26. The air gap or the distance element can have a thickness between 0.5 cm and 1.5 cm, in particular of 1 cm.

The shielding element 30 comprises a U-shaped cross-section 36. The open side 37 of the U-shaped cross-section 36 is arranged in the direction of the internal volume 6, pointing toward the patient receptacle 5, therefore. This has the advantage that the closed side 38 of the U-shaped cross-section 36 opposing the open side 37 is arranged at a greater distance from the internal volume 6 or a field of view in the patient receptacle 5. This reduces the effect, which the shielding element 30 has on the formation of the magnetic field in particular in the field of view.

The legs 39 of the U-shaped cross-section 36 can have in each case a length between 5 cm and 25 cm, in particular of 10 cm, in the radial direction r of the coil rings 3, 4. The open side 37 and the closed side 38 opposing the open side can also have in each case an extension between 5 cm and 25 cm, in particular of 10 cm, in the longitudinal direction. The length of the shielding element 30 along the circumferential direction or tangentially to the circumferential direction, orthogonally to the drawing plane in FIG. 3 therefore, is longer than the legs 39 and longer than the open side 37 and the closed side 38. The length of the shielding element in the circumferential direction or tangentially to the circumferential direction can be between 5 cm and 50 cm, in particular 25 cm. The shielding element 30 can be made at least partially from iron, in particular constructional steel. The material thickness of the shielding element 30 can be between 5 mm and 38 mm, in particular 10 mm.

Figure 7:
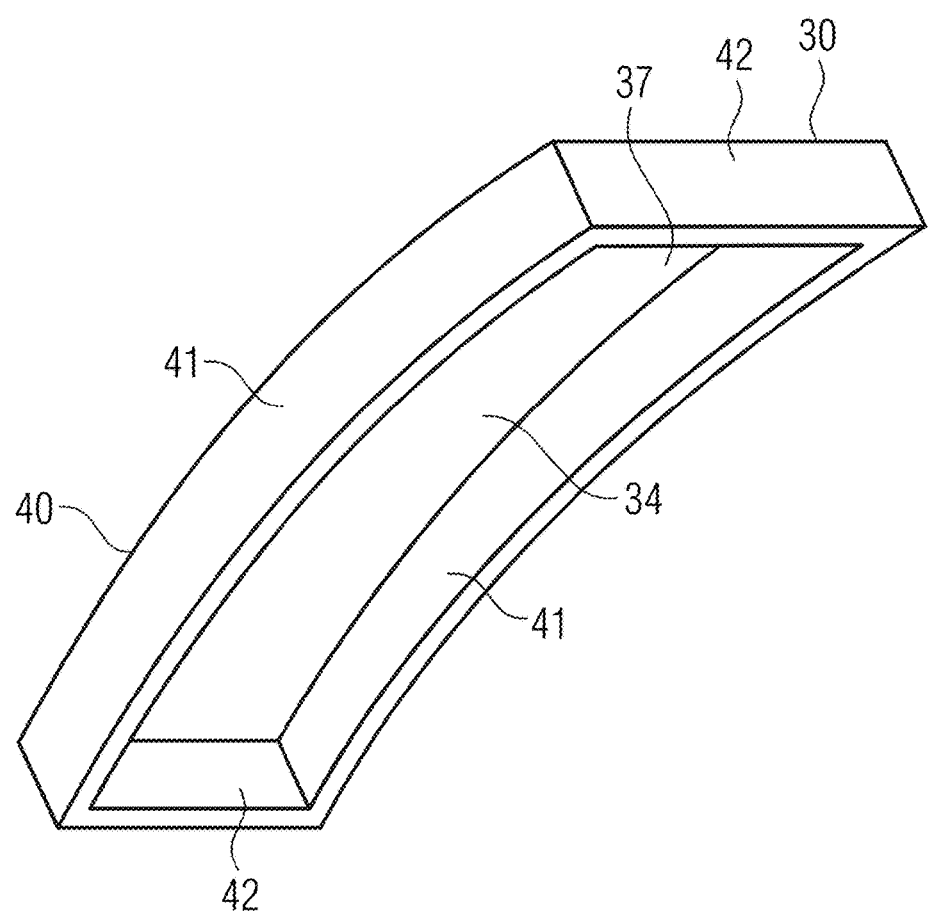
FIG. 7 shows a perspective view of a further example embodiment of a shielding element of the magnetic resonance imaging facility.
Figure 7:

FIG. 7 illustrates a perspective view of a further example embodiment of a shielding element 30. The shielding element 30 has a base section 40 and four wall sections 41, 42, which form a trough shape of the shielding element. The base section 40 is bent along the circumferential direction U, with the wall sections 41, 42 adjoining at the concave side of the base section 40. The base section 40 and the wall sections 41, 42 surround the shielding volume 34 of the shielding element 30 with the exception of the open side 37 of the shielding element 30 opposing the base section 40.

The length of the wall sections 41 in the radial direction r and in the longitudinal direction z can be between 5 cm and 25 cm, in particular 10 cm. The length of the wall sections 42 and of the base section 40 in the longitudinal direction z can also be between 5 cm and 25 cm, in particular 10 cm. The base section 40 and the wall sections 41 can have an extension between 5 cm and 50 cm, in particular of 25 cm, in the circumferential direction U, with the shielding element being longer in the circumferential direction U in particular than in the radial direction r and the longitudinal direction z.

Alternatively it is possible that the base section 40 is also straight, so it extends tangentially to the circumferential direction U and a box shape of the shielding element 30 results. In addition or alternatively, the extension of the shielding element 30 in the circumferential direction or tangentially to the circumferential direction can at least substantially correspond to the extension of the shielding element in the longitudinal direction, so a cup shape of the shielding element 30 results.

Although the invention has been illustrated and described in detail by the preferred example embodiment it is not limited by the disclosed examples and a person skilled in the art can derive other variations herefrom without departing from the scope of the invention.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An electric circuit arrangement for energizing a magnet of a magnetic resonance imaging apparatus, the electric circuit arrangement comprising:
    a first circuit to generate a direct voltage as a DC link voltage from an alternating voltage;
    a second circuit configured as a current source fed by the DC link voltage, the second circuit including
        a down converter to generate a primary current from the DC link voltage, the down converter having a first inductor,
        a transformer to generate a secondary current from the primary current, the transformer having a primary side, a secondary side and a primary coil, the primary coil having a second inductor,
        a switching device to receive the primary current and to output the primary current in different flow directions to the primary side of the transformer, and
        a rectifier to generate a rectified secondary current to energize the magnet, the rectifier being connected to the secondary side of the transformer; and
    at least one control device to control the switching device to output the primary current in a different flow direction to the primary side of the transformer, wherein the first inductor is larger than the second inductor.

2. The electric circuit arrangement of claim 1, wherein the switching device is a full bridge, the full bridge is configured to output the primary current to the primary side of the transformer via a bride section of the full bride, and the full bridge is connected to the down converter.

3. The electric circuit arrangement of claim 2, wherein at least one of an amperage of the secondary current is higher than an amperage of the primary current, or the transformer includes two secondary coils connected to the rectifier.

4. The electric circuit arrangement of claim 2, further comprising:

a first current measuring device to measure the primary current; and a second current measuring device to measure the rectified secondary current, wherein the at least one control device is configured to actuate the down converter as a function of at least one first measured value of the primary current and at least one second measured value of the secondary current.

5. The electric circuit arrangement of claim 1, wherein the at least one control device is configured to control the switching device to output the primary current alternately in the different flow directions to the primary side of the transformer.

6. The electric circuit arrangement of claim 5, wherein the switching device is a full bridge, the full bridge is configured to output the primary current to the primary side of the transformer via a bridge section of the full bridge, and the full bridge is connected to the down converter.

7. The electric circuit arrangement of claim 1, wherein at least one of an amperage of the secondary current is higher than an amperage of the primary current, or the transformer includes two secondary coils connected to the rectifier.

8. The electric circuit arrangement of claim 7, wherein the at least one control device is configured to control the switching device to output the primary current alternately in the different flow directions to the primary side of the transformer.

9. The electric circuit arrangement of claim 1, further comprising:

a first current measuring device to measure the primary current; and a second current measuring device to measure the rectified secondary current, wherein the at least one control device is configured to actuate the down converter as a function of at least one first measured value of the primary current and at least one second measured value of the secondary current.

10. The electric circuit arrangement of claim 9, wherein the at least one control device is configured to regulate the primary current as a function of the at least one first measured value, and adaptively track the primary current as a function of the at least one second measured value.

11. A magnetic resonance imaging apparatus comprising:

an electric circuit arrangement to energize a magnet of the magnetic resonance imaging device, the electric circuit arrangement including a first circuit to generate a direct voltage as a DC link voltage from an alternating voltage, a second circuit configured as a current source fed by the DC link voltage, the second circuit including a down converter to generate a primary current from the DC link voltage, the down converter having a first inductor, a transformer to generate a secondary current from the primary current, the transformer having a primary side, a secondary side and a primary coil, the primary coil having a second inductor, a switching device to receive the primary current and configured to output the primary current in different flow directions to the primary side of the transformer, and a rectifier to generate a rectified secondary current to energize the magnet, the rectifier being connected to the secondary side of the transformer, and at least one control device to control the switching device to output the primary current in a different flow direction to the primary side of the transformer, wherein the first inductor is larger than the second inductor.

12. The magnetic resonance imaging apparatus of claim 2, wherein the magnet is connected to the second circuit.

13. The magnetic resonance imaging apparatus of claim 12, further comprising:

a patient receptacle extending in a longitudinal direction, a magnetic shielding element, and a coil arrangement including at least two coil rings, the at least two coil rings being offset along the longitudinal direction, the coil arrangement being configured to generate a magnetic field in an internal volume, the internal volume being partially surrounded by the at least two coil rings and at least partially including the patient receptacle, wherein the magnetic shielding element and at least one electric component of the second circuit are arranged outside of the internal volume and centrally between the at least two coil rings in the longitudinal direction, and the magnetic shielding element is configured to shield the at least one electric component from the magnetic field.

14. The magnetic resonance imaging apparatus of claim 11, wherein the second circuit is at least one of in a housing of the magnetic resonance imaging apparatus or on the housing of the magnetic resonance imaging apparatus.

15. The magnetic resonance imaging apparatus of claim 11, further comprising:

a patient receptacle, extending in a longitudinal direction, a magnetic shielding element, and a coil arrangement including at least two coil rings, the at least two coil rings being offset along the longitudinal direction, the coil arrangement being configured to generate a magnetic field in an internal volume, the internal volume being partially surrounded by the at least two coil rings and at least partially including the patient receptacle, wherein the magnetic shielding element and at least one electric component of the second circuit of the electric circuit arrangement are arranged outside of the internal volume, and centrally between the at least two coil rings in the longitudinal direction, and the magnetic shielding element is configured to shield the at least one electric component form the magnetic field.

16. The magnetic resonance imaging apparatus of claim 15, wherein the magnetic shielding element includes a U-shaped cross-section, and the magnetic shielding element surrounds a shielding volume on three sides.

17. The magnetic resonance imaging apparatus of claim 16, wherein
an open side of the U-shaped cross-section is adjacent to the internal volume, or
an open side of the magnetic shielding element, is adjacent to the internal volume.

18. The magnetic resonance imaging apparatus of claim 15, wherein
the magnetic shielding element is cup-shaped, box-shaped or trough-shaped,
the magnetic shielding element includes an open side, and
the magnetic shielding element completely surrounds a shielding volume.

19. The magnetic resonance imaging apparatus of claim 15, wherein
the magnetic shielding element is longer in a circumferential direction of the at least two coil rings than in at least one of the longitudinal direction or a radial direction of the at least two coil rings, or
the magnetic shielding element is longer in a direction tangential to the circumferential direction of the at least two coil rings than in the at least one of the longitudinal direction or the radial direction of the at least two coil rings.

* * * * *